US010087233B2

(12) United States Patent
Saint-Remy

(10) Patent No.: US 10,087,233 B2
(45) Date of Patent: Oct. 2, 2018

(54) COAGULATION FACTOR VIII WITH REDUCED IMMUNOGENICITY

(71) Applicant: IMNATE SARL, Strassen (LU)

(72) Inventor: Jean-Marie Saint-Remy, Grez-Doiceau (BE)

(73) Assignee: Imnate Sarl, Strassen (LU)

( * ) Notice: Subject to any disclaimer, the term of this patent is extended or adjusted under 35 U.S.C. 154(b) by 0 days.

(21) Appl. No.: 14/402,922

(22) PCT Filed: May 21, 2013

(86) PCT No.: PCT/EP2013/060397
§ 371 (c)(1),
(2) Date: Nov. 21, 2014

(87) PCT Pub. No.: WO2013/174805
PCT Pub. Date: Nov. 28, 2013

(65) Prior Publication Data
US 2015/0087593 A1    Mar. 26, 2015

(30) Foreign Application Priority Data

May 22, 2012    (EP) .................................... 12168800

(51) Int. Cl.
C07K 14/755    (2006.01)
A61K 38/37    (2006.01)

(52) U.S. Cl.
CPC ............ *C07K 14/755* (2013.01); *A61K 38/37* (2013.01); *A23V 2200/218* (2013.01); *A61M 2202/0452* (2013.01); *Y10S 514/834* (2013.01)

(58) Field of Classification Search
None
See application file for complete search history.

(56) References Cited

U.S. PATENT DOCUMENTS

| | | | | |
|---|---|---|---|---|
| 5,859,204 A | * | 1/1999 | Lollar .................. | C07K 14/755 435/69.1 |
| 7,084,251 B1 | * | 8/2006 | Lawn ................... | C07K 14/745 530/350 |
| 2003/0068785 A1 | * | 4/2003 | Lollar .................. | C07K 14/755 435/69.6 |
| 2009/0118184 A1 | | 5/2009 | Fay et al. | |
| 2010/0233119 A1 | | 9/2010 | Josephson | |
| 2011/0217284 A1 | * | 9/2011 | Seifried ................ | C12N 9/644 424/94.64 |

FOREIGN PATENT DOCUMENTS

| | | | | |
|---|---|---|---|---|
| EP | 1495052 B1 | 10/2008 | | |
| RU | 2423380 C2 | 7/2011 | | |
| WO | WO1995006737 | * 3/1995 | ............. | C12N 15/62 |
| WO | WO 2003/087161 A1 | 10/2003 | | |
| WO | WO2003087161 A1 | * 10/2003 | ........... | C07K 14/755 |
| WO | WO 2006/103298 A2 | 10/2006 | | |
| WO | WO 2009/058466 A1 | 5/2009 | | |
| WO | WO2011060371 A2 | * 5/2011 | ............. | A61K 38/37 |
| WO | WO 2012/069575 A1 | 5/2012 | | |

OTHER PUBLICATIONS

Shen et al. The tertiary structure and domain organization of coagulation factor VIII. Blood. 2008;111:1240-1247.*
European Patent Office, International Search Report in International Application No. PCT/EP2013/060397.
Swaroop, Manju, et al. "Mutagenesis of a potential immunoglobulin-binding protein-binding site enhances secretion of coagulation factor VIII." *Journal of Biological Chemistry* 272.39 (1997): 24121-24124.
Ramezani, Ali, and Robert G. Hawley. "Correction of murine hemophilia A following nonmyeloablative transplantation of hematopoietic stem cells engineered to encode an enhanced human factor VIII variant using a safety-augmented retroviral vector." *Blood* 114.3 (2009): 526-534.
Herzog, Roland W., and Eric Dobrzynski, "Immune implications of gene therapy for hemophilia." *Seminars in thrombosis and hemostasis*. vol. 30. No. 02. 215-225.

* cited by examiner

*Primary Examiner* — Marcela M Cordero Garcia
*Assistant Examiner* — Jia-Hai Lee
(74) *Attorney, Agent, or Firm* — Leydig, Voit & Mayer, Ltd.

(57) ABSTRACT

The invention describes factor VIII molecules with reduced capacity to elicit activation of NKT cells for use in the treatment of congenital and/or acquired haemophilia A and in bleeding disorders. Said factor VIII molecule is obtainable by:
a. identification of at least one NKT cell epitope wherein said epitope comprises hydrophobic aminoacid residues in position P1 and/or P7
b. modification of said epitope(s) by eliminating at least one hydrophobic aminoacid residue in position P1 and/or P7, substituting at least one hydrophobic aminoacid residue in position P1 and/or P7 with a non-hydrophobic residue, or adding a non-hydrophobic residue in position P1 and/or P7.

4 Claims, 7 Drawing Sheets

Specification includes a Sequence Listing.

COAGULATION FACTOR VIII WITH REDUCED IMMUNOGENICITY

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 1,406 bytes (Text) file named "512194_ST25.TXT" created Nov. 19, 2014.

FIELD OF THE INVENTION

The present invention relates to molecules of coagulation factor VIII with reduced or lack of immunogenicity and their use in the therapy of coagulation disorders and in particular in the treatment of type A hemophilia.

BACKGROUND OF THE INVENTION

Factor VIII is a coagulation factor acting as a co-factor in the generation of thombin, an essential component of coagulation. In the absence or insufficiency of functional factor VIII, individuals suffer from bleeding disorders, collectively called hemophilia A. There are two types of hemophilia A, depending from its origin, either genetic (spontaneous hemophilia) or acquired (acquired or autoimmune hemophilia). Spontaneous hemophilia A is a disease affecting males due the location of the factor VIII gene on the X chromosome. Women are carriers but do not suffer from bleeding disorders because of the presence of 2 X chromosomes. Spontaneous hemophilia is further divided into 3 subsets of patients, defined according to the level of circulating factor VIII: severe hemophilia (less than 1% factor VIII), mild hemophilia (1 to 5% factor VIII) and moderate (factor VIII concentrations between 5 and 10%).

Patients suffering from hemophilia require a substitution therapy by factor VIII. This is a continuing therapy for severe hemophilia A patients due to the increased risk of spontaneous, sometimes life-threatening bleeding, or intermittent in mild or moderate hemophilia patients in whom factor VIII is required when there is a trauma or surgery and an acute demand of increased factor VIII concentrations.

By far the main complication patients suffering from hemophilia A have to face is the emergence of antibodies towards the therapeutic agent (factor VIII) used to restore a functional coagulation.

There are currently 2 types of factor VIII used for replacement therapy, plasma-derived and recombinant. Plasma-derived factor VIII is produced from pools of human plasma and contains additional proteins and in particular the physiological chaperon of factor VIII, von Willebrand factor. Recombinant factor VIII is produced by genetic engineering and production by cells of animal or of human origin. Recombinant factor VIII is pure and do not contain von Willebrand factor. Vivid controversy is ongoing to decide whether there is a significant difference in the risk of eliciting an anti-factor VIII immune response when using either plasma-derived or recombinant factor VIII molecule. Whatever the situation, on average 25% of patients receiving factor VIII as a therapeutic agent raise antibodies which inhibit the activity of the replacement agent. Such antibodies are called factor VIII inhibitors.

There is no cure for factor VIII inhibitors. On empirical grounds, it has been demonstrated that the administration of very high doses of factor VIII on a daily basis can result in some cases in a disappearance of inhibitors. This therapy, called induction of immune tolerance, is not reliable in its success. The lack of surrogate markers able to predict the outcome of immune tolerance de facto limits its use in an attempt to eliminate the formation of factor VIII inhibitors. Moreover, the prohibitive cost related to tolerance induction is such that only a few patients can be considered for tolerance induction.

Factor VIII inhibitors are high-affinity specific antibodies, which implies the participation of T lymphocytes in their formation. The consequence of this is that the immune response is fully memorized, leaving populations of memory B cells, which upon stimulation, transform into plasmocytes producing antibodies, and memory T cells which maintain the capacity to mount further antibody response upon each subsequent exposure to factor VIII. Patients presenting with factor VIII inhibitors can not be treated with factor VIII not only because inhibitors neutralize factor VIII function and, likely, increase the clearance rate of factor VIII, but also because each further exposure to factor VIII increases the concentrations of such inhibitors.

Patent application WO 2009/101206 describes a method by which it is possible to eliminate the production of inhibitors by acting at the level of adaptive immunity, namely at the level of the interaction between factor VIII-specific T and B cells. This application describes how the risk of producing new inhibitors upon factor exposure can be eliminated, but also how existing inhibitors can be eradicated. However, we have unexpectedly discovered that factor VIII is a very potent activator of the innate immunity, which appears to be a pre-requisite for eliciting an adaptive response and inhibitors. Given that factor VIII has to be administered on a regular basis (e.g. 2 or 3 times a week for severe hemophilia A patients), and that therefore the risk of eliciting a new production of factor VIII inhibitors persists, there is an urgent need to define methods by which therapeutic factor VIII molecules could be produced, which have lost their capacity to activate the innate immunity.

The PCT application PCT/EP2011/070911 describes methods by which proteins with capacity to activate NKT cells can be transformed so as to loose such a capacity. Thus, NKT cells are part of the innate immune system, which is conventionally defined as lacking memorization. However, as described in PCT application PCT/EP2011/070911 NKT cells can recognize and be activated by the presentation of hydrophobic peptides by the CD1d molecule. As the peptide is derived from an antigen for which NKT cells are specific, this represent an antigen-specific innate immune system activation. The above-mentioned PCT application describes methods by which proteins showing the property to activate antigen-specific NKT cells can be modified by aminoacid substitution or deletion, thereby eliminating the capacity to bind to CD1d.

The present invention describes molecules of factor VIII obtained by the methodology described in PCT application PCT/EP2011/070911 which have lost their capacity to activate the innate immune system and, consequently, show a lack or significantly reduced capacity to active an adaptive immune response with production of inhibitors. The invention further describes the use of such factor VIII molecules for the treatment of patients in need for replacement therapy, and in particular severe hemophilia A patients. The present invention also discloses methods in which gene therapy using factor VIII molecules of the present invention can be used.

SUMMARY OF THE INVENTION

The present invention relates to the production of molecules of factor VIII with reduced immunogenicity.

The present invention also relates to the use of said factor VIII molecules for the treatment of patients in need for said treatment.

The PCT application PCT/EP2011/070911 describes methods to obtain peptides or polypeptides with reduced capacity to activate NKT cells. Thus, we made the unexpected finding that a significant proportion of peptides or polypeptides carried aminoacid sequences which allow them to bind and to be presented by CD1d determinants for activation of natural killer T (NKT) cells. Activation of such cells results in release of cytokines and, in some cases, in acquisition of, or increase in cytolytic properties.

The present invention relates in one aspect to the use of at least one isolated polypeptide used as an allofactor, which has been modified to eliminate at least one hydrophobic amino acid residue involved in the formation of an epitope recognized by NKT cells, for the manufacture of a medicament for preventing in a subject immune responses to said allofactor.

More specifically, the present invention relates to factor VIII and use of factor VIII as a medicament. Factor VIII is a co-factor of the coagulation system which participates to activation of thrombin by facilitating the formation of tenase, a serine esterase which assembles factor VIII, factor IX and factor X. Factor X carries the enzymatic activity converting thrombin. In the absence of factor VIII, the rate of tenase formation is drastically reduced, leaving the patients at risk of spontaneous bleedings, which are often life-threatening, and requires prompt therapeutic measures. When the concentration of factor VIII is moderately reduced (between 5 and 10%), the patients usually bleed only under trauma or surgery.

Patients suffering from severe hemophilia A (less than 1% factor VIII) have frequent spontaneous bleedings and require prophylactic treatment either on continuous administration or bolus injection 2 or 3 times a week. In addition, patients in whom an increased catabolism of factor VIII is observed, as in septic shock, acute fibrinolysis, polytrauma or cerebral hemorrhage, are also in need for factor VIII administration.

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification. The term "polypeptide" when used herein refers to generally longer peptides or proteins.

The term "epitope" when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "T cell epitope" or "T-cell epitope" in the context of the present invention refers to a dominant, sub-dominant or minor T cell epitope, i.e., a part of an antigenic protein that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term "NKT cell epitope" refers to a part of an antigenic protein that is specifically recognized and bound by a receptor at the cell surface of a T lymphocyte. In particular, a NKT cell epitope is an epitope bound by CD1d molecules.

The term "CD4+ effector cells" refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term "NKT cells" refers to cells of the innate immune system characterized by the fact that they recognize epitopes presented by the CD1d molecule. In the context of the present invention, NKT cells can belong to either the type 1 (invariant) subset (iNKT), or any other subset which would be activated by presentation of peptidic epitopes by CD1d. The term "NKT cells" also includes NKT cells belonging to either the CD4 or CD8 lineage. NKT cells often carry receptors such as NK1.1 and NKG2D.

The "CD1d molecule" refers to a non-MHC derived molecule made of 3 alpha chains and an anti-parallel set of beta chains arranged into a deep hydrophobic groove opened on both sides and capable of presenting lipids, glycolipids or hydrophobic peptides to NKT cells.

The term "immune disorders" or "immune diseases" refers to diseases wherein a reaction of the immune system is responsible for or sustains a malfunction or non-physiological situation in an organism. Immune disorders in the context of the present invention refer to pathology induced by infectious agents and tumor surveillance.

The term "allofactor" or "alloantigen" refers to a protein, peptide or factor (i.e. any molecule) displaying polymorphism when compared between two individuals of the same species, and, more in general, any protein, peptide or factor that induces an (alloreactive) immune response in the subject receiving the allofactor. By extension, allofactors also include genetically-modified proteins used for feeding.

DETAILED DESCRIPTION

Figure 1:
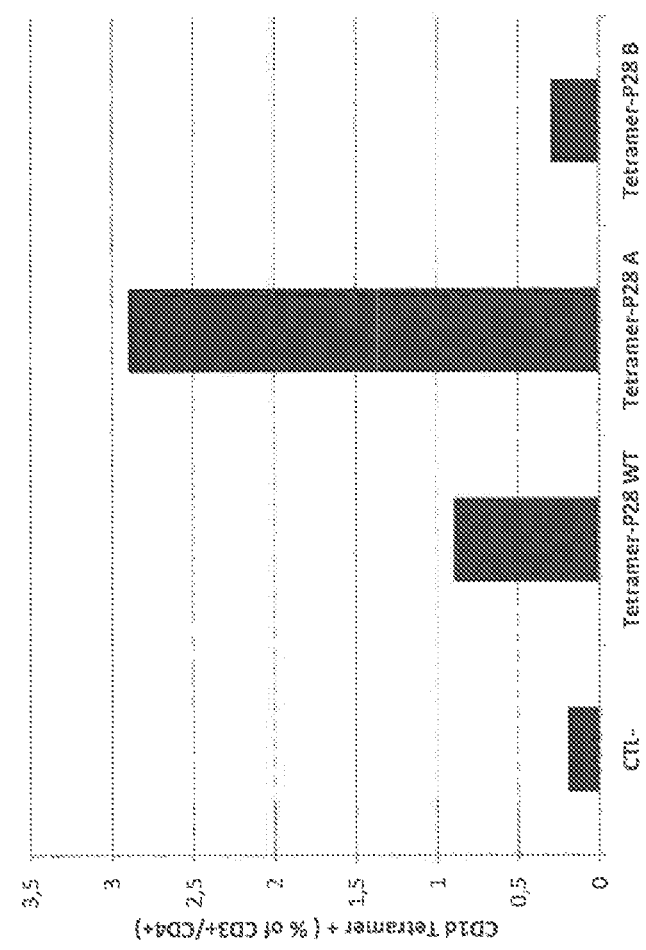
FIG. 1 is a graph of CD1d+ cells (%) plotted for indicated samples.

The present invention provides factor VIII molecules to prevent in a subject an immune response towards said factor VIII molecules.

Factor VIII has a mature sequence made of 2332 amino acids with a domain structure A1-a1-A2-a2-B-a3-A3-C1-C2, in which A1, A2, B, A3, C1 and C2 represent domains and a1, a2 and a3 represent acidic regions linking said domains. Upon proteolytic processing, which occurs after secretion, factor VIII is present in plasma under a major form consisting of variable length of A1-a1-A2-a2-B (the length is conditioned by the length of the B domain) linked noncovalently to light chains consisting of A3-C1-C2.

FVIII accelerates the activation of factor X by factor IX on a suitable phospholipid surface, thereby amplifying the clotting process. The active form of factor VIII is made of a heterotrimer consisting in A1-a1, A2-a2 and A3-C1-C2.

In particular, the invention provides ways to prevent the expansion and functional activity of NKT cells. Such cells are usually classified into distinct subsets, namely type 1 for NKT cells carrying an invariant TCR alpha chain (Valpha14 in the mouse, Valpha24 in humans), or type 2 NKT cells which present with a diverse alpha chain repertoire and is deemed to be specific for sulfatides. However, recent evidence has suggested that alternative subsets of NKT cells which do not fit in the type 1 or type 2 category. It is the purpose of the present invention to include these non conventional NKT cells, which can carry either the CD4 or the CD8 co-receptor. Upon presentation of an antigen bound to CD1d, NKT cells are rapidly activated and secrete a number of cytokines thought to be determinant to influence other cells from both the innate and adaptive immune systems. In some circumstances, said activated NKT cells acquire or increase cytotoxic properties.

In the context of the present invention, we made the unexpected observation that peptides can be presented by the CD1d molecule. A characteristic of the CD1d molecule is that it is made of two anti-parallel alpha chains forming a cleft sitting atop of a platform made of two anti-parallel beta chains. The cleft is narrow and deep and accept only hydrophobic residues, classically deemed to be only lipids. The cleft can accommodate a sequence of 7 aminoacids characterized as a hydrophobic residue in position (P)1 and 7, and an aliphatic residue in P4. P1 is an obligate hydrophobic residue, such as F, W, H or Y. However, P7 is permissive and can contain alternative residues provided they are not polar. Residues in P4 are preferably aliphatic but is optional. A general sequence for a CD1d binding motif is therefore [FWTHY]-$X_2X_3$-[ILMV]-$X_5X_6$-[FWTHY] (SEQ ID NO: 7). It should however be clear for those skilled in the art that the motif is symmetrical and that P7 can be considered as P1, and P1 can be considered as P7. The general sequence of a CD1d binding motif is provided here as a general indication without any limiting intention.

The present invention relates to the production of factor VIII molecules and method thereof, said molecules containing CD1d binding motif(s), which confer them with the capacity to activate NKT cells and which are modified by elimination and/or substitution of hydrophobic residues in P1 and/or P7 with a non-hydrophobic residue, with the proviso that F in position 309 is not substituted by S and H in position 317 is not substituted by A, and/or adding a non-hydrophobic residue in position P1 and/or P7, with, optionally, substitution or deletion of aliphatic residues in P4, or any combination of these, which results in a loss or significant reduction of the capacity of peptides or polypeptides to bind to CD and thereby results in a loss or significant reduction of said peptides or polypeptides to activate NKT cells.

The present invention therefore relates to a factor VIII molecule with a domain structure A1-a1-A2-a2-B-a3-A3-C1-C2, in which A1, A2, B, A3, C1 and C2 represent domains and a1, a2 and a3 acidic regions linking said domains said factor VIII molecule having a reduced capacity to activate NKT cells, said factor VIII molecules is obtainable by:

a. identification of at least one NKT cell epitope wherein said epitope comprises hydrophobic aminoacid residues in position P1 and/or P7 b. modification of said epitope(s) by eliminating at least one hydrophobic aminoacid residue in position P1 and/or P7, substituting at least one hydrophobic aminoacid residue in position P1 and/or P7 with a non-hydrophobic residue, or adding a non-hydrophobic residue in position P1 and/or P7.

The present invention also relates to methods to obtain a factor VIII molecule with reduced capacity to activate NKT cells comprising the steps of:

a. identification of at least one NKT cell epitope wherein said epitope comprises hydrophobic aminoacid residues in position P1 and/or P7 b. modification of said epitope(s) by eliminating at least one hydrophobic aminoacid residue in position P1 and/or P7, substituting at least one hydrophobic aminoacid residue in position P1 and/or P7 with a non-hydrophobic residue or adding a non-hydrophobic residue in position P1 and/or P7.

In a more particular embodiment, F, W, T, H or Y in positions P1 and/or P7 are replaced by a non-hydrophobic aminoacid residue, or, optionally, I, L, M or V in position P4 is replaced by a non-aliphatic residue, or any combination of these.

In yet another particular embodiment, hydrophobic residues located in position P1 and/or P7, or, optionally, aliphatic residues located in P4, or any combination of these, are replaced by at least one non-natural aminoacid different from non-natural F, W, T, H, Y, or by a non-aromatic organic compound.

In yet another particular embodiment at least one aminoacid is added within the CD1d binding motif, in any location within the P1 to P7 sequence, which disrupts the motif, prevents its capacity to bind to CD1d and thereby its capacity to activate NKT cells.

In a preferred embodiment, non-natural aminoacids are D-aminoacids.

The present invention also relates to the factor VIII molecules containing CD1d binding motif(s), which confer them with the capacity of activate NKT cells, and which are modified by eliminating at least one hydrophobic aminoacid residue in position P1 and/or P7, substituting at least one hydrophobic aminoacid residue in position P1 and/or P7 with a non-hydrophobic residue, or adding a non-hydrophobic residue in position P1 and/or P7, and additionally, by deletion of aliphatic residues in P4, or any combination of these, which results in a loss or significant reduction of the capacity of peptides or polypeptides to bind to CD and thereby results in a loss or significant reduction of said peptides or polypeptides to activate NKT cells.

Upon administration to a subject, such factor VIII molecules are not loaded on CD and thereby are prevented from activating NKT cells.

In a further aspect, the invention also covers the use of factor VIII molecules comprising at least one substitution or deletion of F, W, T, H or Y in positions P1 or P7 for preventing in a subject an immune response towards factor VIII.

In yet a further aspect, the invention covers the use of factor VIII molecules comprising at least one substitution or deletion of F, W, T, H or Y in positions P1 or P7 for preventing in a subject the activation of NKT cells towards factor VIII.

In yet a further aspect, the invention also covers the use of factor VIII molecules comprising at least one substitution or deletion of F, W, T, H or Y in positions P1 or P7 for the manufacture of a medicament for preventing in a subject an immune response towards factor VIII.

The number of CD1d binding motifs when present in a peptide or polypeptide, is very limited. Examples of such peptides or polypeptides are provided below for factor VIII. Typically a polypeptide presents one to five of these motifs.

An additional advantage of the present invention is that the CD1d molecule presents a very limited degree of polymorphism. It is therefore obvious for the one skilled in the art that the same aminoacid substitutions, addition or deletions according to the present invention provide peptides or polypeptides useful for all or a large majority of subjects. This is in sharp contrast with peptide or polypeptide motifs binding to MHC class II molecules, wherein a large number of peptides can be delineated which contain the appropriate sequence. This is due to the minimum constraints imposed to MHC class II binding peptides and to the large polymorphism of class II molecules.

Factor VIII molecules which are the object of the present invention are identified as follows:

(1) optionally, the aminoacid sequence of factor VIII is evaluated for the presence of at least one CD motif containing an hydrophobic residue in P1 and P7, and an aliphatic residue in P4. A general sequence such as [FWTHY]-$X_2X_3$-[ILMV]-$X_5X_6$-[FWTHY] (SEQ ID NO: 7) can be used for using algorithms well known in the art such as http://expasy.org/tools/scanprosite/

This general sequence should be considered as a tool to help identifying which sequence(s) in said peptide or polypeptide contain a motif which could enable said peptide or polypeptide to activate NKT cells.

(2) the capacity of the peptide or polypeptide to bind to CD1d is tested in vitro using a cell line expressing the CD1d molecule. Examples of such cell lines are known in the art and used to produce examples in the present application (for instance, JAWS2 cells and U937 cells). In a preferred embodiment, the cell line is not presenting MHC class II molecules and is transduced for hyperexpression of CD1d using a viral vector containing the DNA sequence of CD1d or any other means known in the art to introduce a gene in a cell. Methods for cell transduction are known in the art. The cell line is loaded in culture with the peptide or polypeptide, or with a synthetic peptide encompassing the corresponding sequence. Such synthetic peptides are easily produced by synthesis, using for instance the fmoc solid phase synthesis well known in the art. Efficient presentation of the peptide, polypeptide or corresponding synthetic peptide by the CD molecule is then evaluated by measuring the activation of NKT cells. Such cells can be obtained from peripheral blood by, for instance, magnetic sorting and maintained in culture, in the presence of cytokines such as IL-2, IL-15 or IL-7. These methods are described in the art (see for instance Godfrey et al, Nature reviews Immunology 2010, 11: 197-206). Activation of NKT cells is assessed using methods such as evaluation of cytokine production.

Alternatively, peptides actually presented by antigen-presenting cells in CD1d molecules can be eluted and separated by various chromatography methods. Full description of such methodology will be found in Scott et al, Immunity, 12: 711-720, 2000. Said peptides are then sequenced to identify which aminoacid residues are located in P1 and P7.

Alternatively, said synthetic peptides can be loaded on dimers, tetramers or polymers of the CD molecule to detect NKT cells specific for such peptide. One possibility is to use fluorescence-labeled tetramers and detection using a fluorescence-activated cell sorting system (facs).

(3) the aminoacid sequences identified as being able to activate NKT cells and, optionally, identified by algorithms, are then modified by either substitution or deletion. In a preferred embodiment, F, W, T, H or Y in positions P1 and/or P7 are replaced by at least one aminoacid different from F, W, T, H, Y. Natural aminoacids can be modified by post-transcriptional modifications or substituted with chemical groups such as methyl groups. In another preferred embodiment, F, W, T, H or Y in positions P1 and/or P7 are replaced by any suitable alternative non-natural aminoacid. Examples of non-natural aminoacid residues are D-aminoacids. In yet another embodiment, F, W, T, H or Y in positions P1 and/or P7 are replaced by at least one aminoacid different from F, W, T, H, Y. In another preferred embodiment, F, W, T, H or Y in position P1 is replaced by at least one aminoacid different from F, W, T, H, Y, by any suitable alternative non-natural aminoacid or by a non-aromatic organic compound. Such aminoacid substitution is obtained using methods well known in the art. In yet a further preferred embodiment, F, W, T, H or Y in position P1 is deleted. In yet another embodiment, F, W, T, H or Y in positions P1 and P7 are deleted. Methods to carry out said deletions are well known in the art. In yet another particular embodiment at least one aminoacid is added within the CD1d binding motif, in any location within the P1 to P7 sequence.

(4) optionally, it may be advantageous to replace hydrophobic aminoacid residues adjacent to the first (P1) and or the last (P7) position by non-hydrophobic residues. Said hydrophobic residues can be located within the flanking regions of the epitope or within the epitope sequence itself at positions P2 or P6). Positions P−2 and P−1, P2 and/or P6, P8 and P9, located at the amino-terminal end or carboxy-terminal end of the epitope, respectively, are advantageously occupied by non-hydrophobic residues, namely aminoacids different from F, W, T, H or Y, which further reduce the affinity of the epitope for CD1 d and thereby the capacity of the epitope to activated NKT cells.

(5) NKT cells are then tested for their reactivity with the peptides modified as described in (3). Alternatively, the full-length protein from which the peptide is derived can be produced with the modification of the sequence as described in (3). Various methods can be used to determine whether NKT cells have lost or have reduced their capacity to react to the modified peptide or protein. These methods are known in the art. Proliferation of NKT cells can be assessed by incorporation of radioactive thymidine, or by evaluating the concentration of cytokines produced in culture medium. Alternatively, NKT cells can be evaluated by ELISPOT using a variety of antibodies directed towards cytokines or molecules associated with the cytolytic properties of the cells, such as granzyme B. Alternatively, NKT cells can be evaluated for early signaling events, such as phosphorylation of Fyn or surface activation markers.

In particular, analysis of the sequence of the A1 domain of factor VIII has identified two regions containing motifs enabling factor VIII to bind to the CD1d molecule, according to the methods described above. These 2 regions encompass aminoacid residues 190 to 209 and 309 to 323 and preferably 309 to 316, with sequence:

```
190-209:  QTLHKFILLFAVFDEGKSWH  (SEQ ID NO: 1)

309-323   FCHISSHQHDGMEAY       (SEQ ID NO: 2)
```

Hydrophobic aminoacid residues are underlined and each of the 2 sequences contain 2 CD1d binding motifs, namely:

H193-F199

F195-V201 (P7 is permissive and can accommodate valine)

F309-H315

H317-Y323

According to the present invention medicaments are envisaged for the treatment of diseases wherein administration of factor VIII is required, such as in congenital or acquired deficiency of factor VIII, and in disorders in which it is beneficial to administer factor VIII, such in bleeding disorders associated with acute consumption of factor VIII as observed in septic shock, polytrauma and acute fibrinolysis, or in uncontrolled bleeding associated with cerebral hemorrhage.

The medicament of the invention is usually, though not necessarily, a (pharmaceutical) formulation comprising as active ingredient at least one of the factor VIII molecules of the invention or a gene therapeutic vector capable of expressing said factor VIII molecules. Apart from the active ingredient(s), such formulation will comprise at least one of a (pharmaceutically acceptable) diluent.

In general, administration of factor VIII molecules of the invention prevents activation of the innate immune system, more particularly activation of NKT cells, more particularly the production of cytokines associated with NKT cell activation.

The identification of a NKT-cell epitope in the context of the present invention is known to a person skilled in the art. For instance, peptide sequences isolated from the factor VIII molecule are tested by, for example, NKT cell biology techniques, to determine whether the peptide sequences elicit a NKT cell response. Those peptide sequences found to elicit a NKT cell response are defined as having NKT cell stimulating activity. Human NKT cell stimulating activity can further be tested by culturing NKT cells obtained from an individual sensitized to factor VIII, and determining whether proliferation of NKT cells occurs in response to the peptide/epitope as measured, e.g., by cellular uptake of tritiated thymidine. Stimulation indices for responses by NKT cells to peptides/epitopes can be calculated as the maximum CPM in response to a peptide/epitope divided by the control CPM. A NKT cell stimulation index (S.I.) equal to or greater than two times the background level is considered "positive." Positive results are used to calculate the mean stimulation index for each peptide/epitope for the group of peptides/epitopes tested. An immunogenic peptide having a NKT cell stimulation index of greater than or equal to 2 is considered useful as a candidate to carry out the substitution or deletion of hydrophobic aminoacid residues as described in the present invention.

A peptide or polypeptide of the invention is said to be of reduced capacity to activate NKT cells when the S.I. is less than two times the background level, or when levels of cytokines produced upon stimulation is less than 50% of that produced when stimulation is carried out with the natural peptide or polypeptide sequence, or when the levels of cytolytic agents such as granzyme B is reduced by at least twofold as compared to peptides or polypeptides of natural sequence.

Soluble CD1d molecules are obtained and made tetrameric by synthesis and/or chemical coupling. The CD1d molecule is purified by affinity chromatography. Soluble CD1d molecules are incubated with a biotin-labeled reference peptide produced according to its strong binding affinity for said CD1d molecule. Peptides to be assessed for CD1d binding are then incubated at different concentrations and their capacity to displace the reference peptide from its CD1d binding site is calculated by addition of neutravidin. Methods can be found in for instance in Texier et al., (2000) *J. Immunology* 164, 3177-3184) for peptides presented by the MHC class II determinants, but the method can easily be applied to CD1d-restricted NKT cell epitopes.

If two or more aminoacid sequences which share an area of overlap in the native peptide or polypeptide sequence are found to have human NKT cell stimulating activity, as determined by T cell biology techniques, mutation or deletion of hydrophobic aminoacid residues may be carried out for residues belonging to one or to both of the sequences.

The route of administration for factor VIII molecules of the present invention may vary according to the indication. Examples are intravenous or subcutaneous injection of factor VIII, but the present invention also covers alternative routes of administration such as intranasal, oral, sublingual, percutaneous or intramuscular.

Factor VIII molecules of the present invention can be produced using methods know in the art for the production of recombinant proteins using expression systems such as bacterial cells, yeast cells, insect cells, plant cells or mammalian cells.

Factor VIII molecules of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frupperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced factor VIII molecules of the invention can be derived from a larger precursor protein, e.g., via enzymatic cleavage of enzyme cleavage sites inserted adjacent to the N- and/or C-terminus of the peptide or polypeptide, followed by suitable purification.

The present invention also relates to nucleic acid sequences encoding the factor VIII molecules of the present invention and methods for their use, e.g., for recombinant expression or in gene therapy. In particular, said nucleic acid sequences are capable of expressing factor VIII molecules of the invention.

In gene therapy, recombinant nucleic acid molecules encoding the factor VIII molecules of the present invention can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cell normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding a factor VIII molecule according to the invention is provided. In particular embodiments, the vector is generated such that the nucleic acid molecule sequence is expressed only in a specific tissue. Methods of achieving tissue-specific gene expression are well known in the art, e.g., by placing the sequence encoding a factor VIII molecule of the invention under control of a promoter, which directs expression of said molecule specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for a peptide or polypeptide according to the invention may be used in gene therapy.

Factor VIII of the present invention can be modified by methods known in the art.

Factor VIII molecules can encompass the entire aminoacid sequence of factor VIII or only parts of it. One example is provided by B domain deleted factor VIII molecules. The B domain is dispensable for the function of factor VIII and can therefore be deleted without affecting factor VIII function. The a2 and a3 domains are usually linked by aminoacid sequence which can be artificial or can represent sequences from the B domain itself. Factor VIII molecules can be modified by addition and/or substitution of aminoacids so as to increase factor VIII stability by, for instance, reducing the decoy rate of the A2 domain, or by increasing factor VIII resistance to proteolytic enzymes. Factor VIII molecules can be stabilized by coupling to Fcgamma part of antibodies, for instance to increase its recycling trough the FcRn receptor. Factor VIII can be stabilized by reducing its degradation using polyethyleneglycol residues (PEG derivatives) or alternative chemical substitution. All these modifications are considered as within the scope of the present invention.

The prior art (Swaroop et al., The Journal of Biological Chemistry, vol 272, pp 24121-24124, 1997; Cerullo et al., Molecular Therapy, vol 15, pp 2080-2087, 2007) has identified that mutation of F309 (SEQ ID NO: 2) increases the rate of production of factor VIII molecules by cells transfected with a factor VIII construct. Cerullo et al. observed a non-significant reduction of the production of inhibitor antibodies in factor VIII KO mice treated with the F309 mutant, teaching away the one skilled in the art from the use of such mutant for reducing factor VIII immunogenicity. Moreover, in said prior art, there is no mention that F309 could be part of a CD1d binding motif.

The medicament of the invention is usually, but not necessarily a (pharmaceutical) formulation comprising as active ingredient at least one factor VIII molecule of the invention, a gene therapeutic vector capable of expressing said factor VIII molecule. Apart from the active ingredient(s), such formulation will comprise at least one of a (pharmaceutically acceptable) diluent. Typically, pharmaceutically acceptable compounds can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated.

The medicament or pharmaceutical composition of the invention may, in a preferred embodiment, need to be administered to a subject in need as part of a prophylactic or therapeutic regimen comprising multiple administrations of said medicament or composition. Said multiple administrations usually occur sequentially and the time-interval between two administrations can vary and will be adjusted to the nature of the active ingredient and the nature of the condition to be prevented or treated. The amount of active ingredient given to a subject in need of a single administration can also vary and will depend on factors such as the physical status of the subject (as for instance weight and age), the status of the condition to be prevented or treated, and the experience of the treating doctor, physician or nurse.

The term “diluents” refers for instance to physiological saline solutions. The term “pharmaceutically acceptable carrier” means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the active ingredients.

The formulations may conveniently be presented in unit dosage form and may be prepared by any of the methods well known in the art of pharmacy.

The following examples are provided here to illustrate the invention. There is however no intention to limit the invention to such examples.

Example 1

Binding of Peptide of SEQ ID NO: 1 to CD1d Tetramers

A peptide encompassing SEQ ID NO: 1 was obtained by chemical synthesis. This peptide was used to load CD1d tetramers (ProImmune) by overnight incubation.

NKT cells were prepared from the spleen of naïve mice by depletion of all CD4(−) cells using magnetic beads.

CD4+ cells were then incubated with CD1d tetramers loaded by peptide of SEQ ID NO: 1 (P28 WT in FIG. 1), which corresponds to aminoacid sequence 190 to 209.

FIG. 1 shows that ±1% of CD4+ T cells were detected. Further, peptide of SEQ ID NO: 1 was separated into 2 parts and synthetic peptides covering the sequence 190-200 (SEQ ID NO: 3, P28 A in FIG. 1) and 200-210 (SEQ ID NO: 4, P28 B in FIG. 1) were produced.

Sequence of peptide of SEQ ID NO: 3 is:
QTLHKFILLFA (corresponding to aminoacid sequence 190 to 200)

Sequence of peptide of SEQ ID NO: 4 is:
AVFDEGKSWHS (corresponding to aminoacid sequence 200 to 210)

The Figure indicates that a major CD1d binding motif is located in SEQ ID NO: 3, and limited though significant % of NKT cells were detected by the peptide of SEQ ID NO: 4.

It was therefore concluded that a major CD binding motif was located in peptide of SEQ ID NO: 3.

Example 2

Activation of NKT Cells by Immunization with JAWS2 Cells Loaded with Peptide of SEQ ID NO: 1

JAWS2 cells express CD1d but not MHC class II determinants. These cells were used to show that the presentation of peptide of SEQ ID NO: 1 can occur via CD1d.

JAWS2 cells were incubated 2 h at 37° C. with peptide of SEQ ID NO: 1 (10 µg/ml) and thoroughly washed twice. Cells were then treated with mitomycin to block cell division and washed 4 times to eliminate mitomycin. A cell suspension containing 2×10⁶ cells in physiological serum was injected by the intraperitoneal route in each of a series of 3 naïve factor VIII KO mice. As a control, 3 naïve factor VIII KO mice received the same number of JAWS2 cells which had not been incubated with peptide of SEQ ID NO: 1.

Five days after IP injection, the mice were sacrificed and their spleen prepared as above using magnetic beads to eliminate all CD4(−) cells.

CD4+ cells were then incubated with tetramers loaded with peptide of SEQ ID NO: 1.

Figure 2:
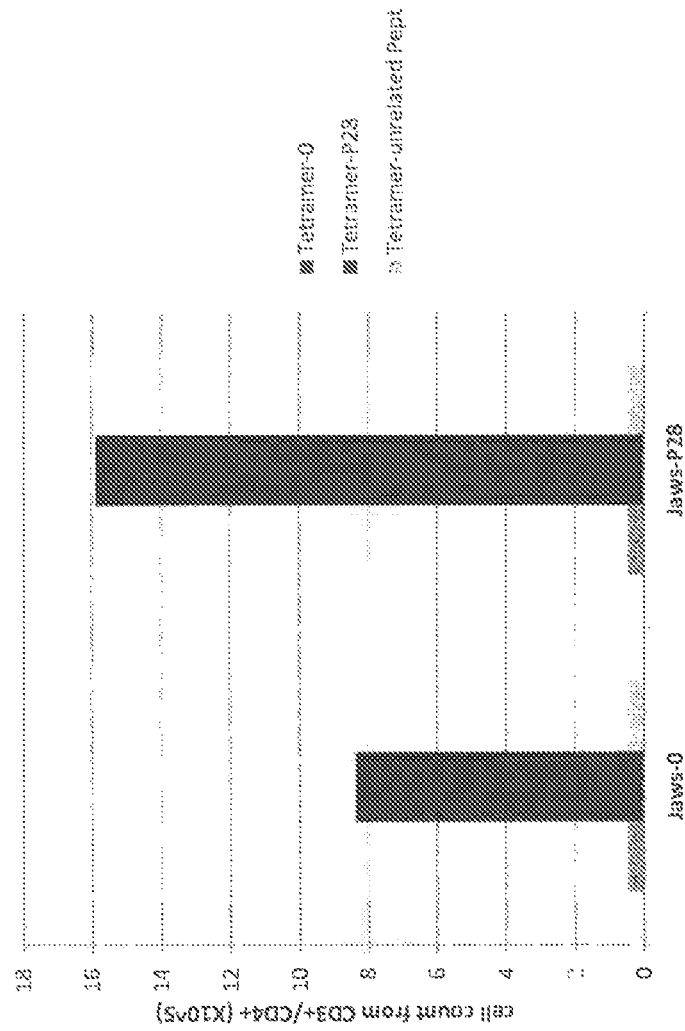
FIG. 2 is a graph of cell count from CD3+/CD4+ plotted for indicated samples.

FIG. 2 shows that a significant proportion of NKT cells (8%) present in the natural repertoire are specific for peptide of SEQ ID NO: 1 and that such proportion is doubled (16%) when peptide of SEQ ID NO: 1 is presented by JAWS2 cells.

The specificity of NKT cell detection is shown by the lack of NKT detection with unloaded tetramers as well as when tetramers were loaded with a peptide unrelated to peptide of SEQ ID NO: 1.

It was therefore concluded that presentation of peptide of SEQ ID NO: 1 occurred via CD1d presentation and that this presentation was sufficient as to bind and activate NKT cells.

Example 3

Administration of Mutated Factor VIII Reduces the Formation of Antibodies to Factor VIII To determine whether mutation aimed at eliminating CD1d binding motifs in factor VIII could reduce the concentration of anti-factor VIII antibodies, wildtype or mutated factor VIII were cloned in the plasmid pGC5AM-EN. Mutations in positions F309 and H315, each time into a alanine, were introduced in the sequence of factor VIII using PCR and the splicing by overlap extension (SOE-PCR) technology.

The plasmids containing either the native or the mutated sequence were checked by sequencing and prepared by maxiprep.

Plasmids (100 µg in 2 ml) were directly administered into naïve factor VIII KO C57BL/6 mice (3 mice per group) using the hydrodynamic pressure method (injection made in less than 7 seconds), known in the art to direct plasmids essentially to the liver. Control mice were injected using the same method but with naked plasmid (n=3).

A total of 3 injections were made at intervals of 10 days.

Ten days after the last injection, plasma concentrations of antibodies to factor VIII and the concentration of antibodies inhibiting the function of factor VIII were measured by ELISA and chromogenic assay, respectively.

Figure 3A:
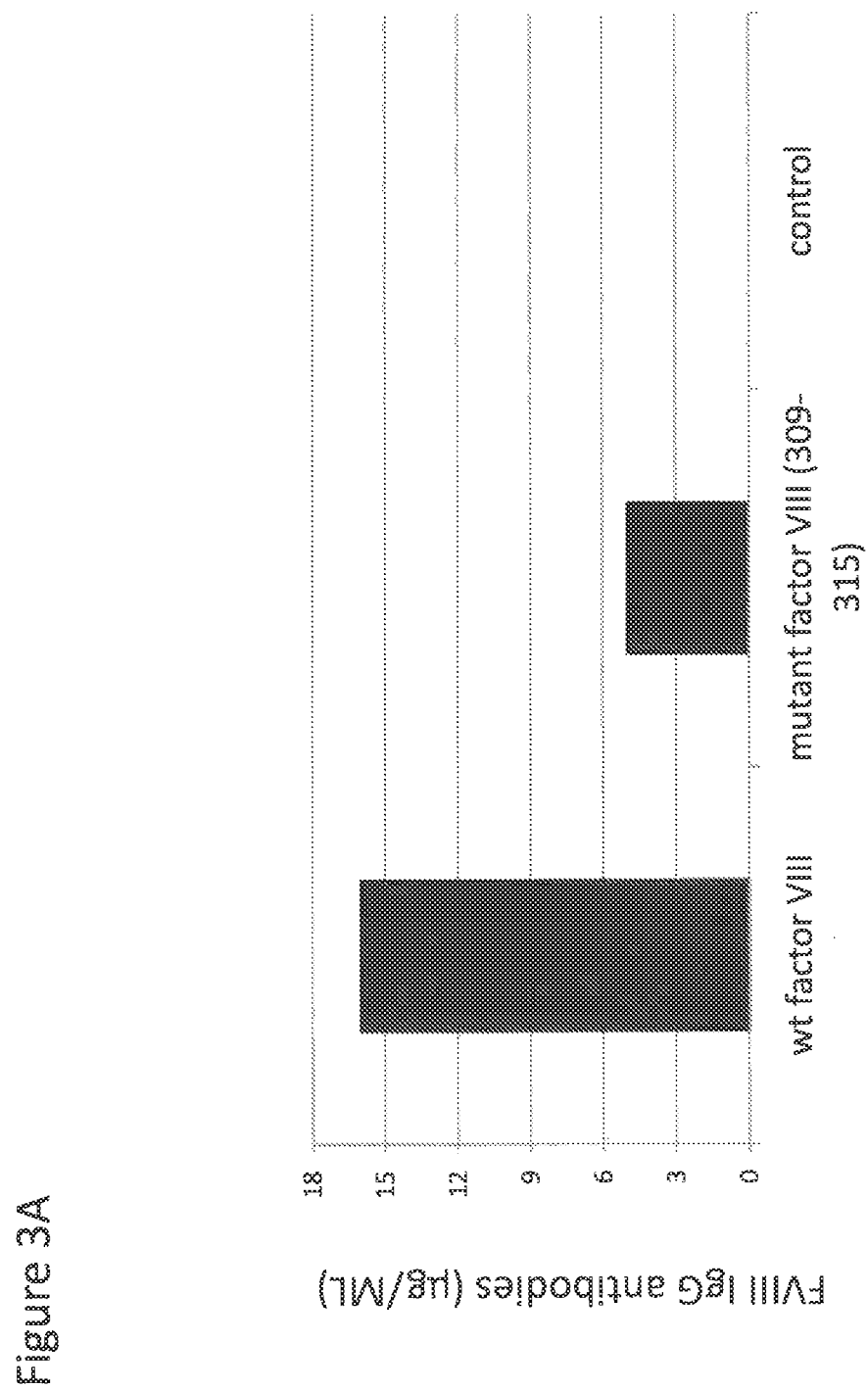
FIG. 3A is a graph of FVII IgG antibodies (µg/ML) plotted for indicated samples.
Figure 3B:
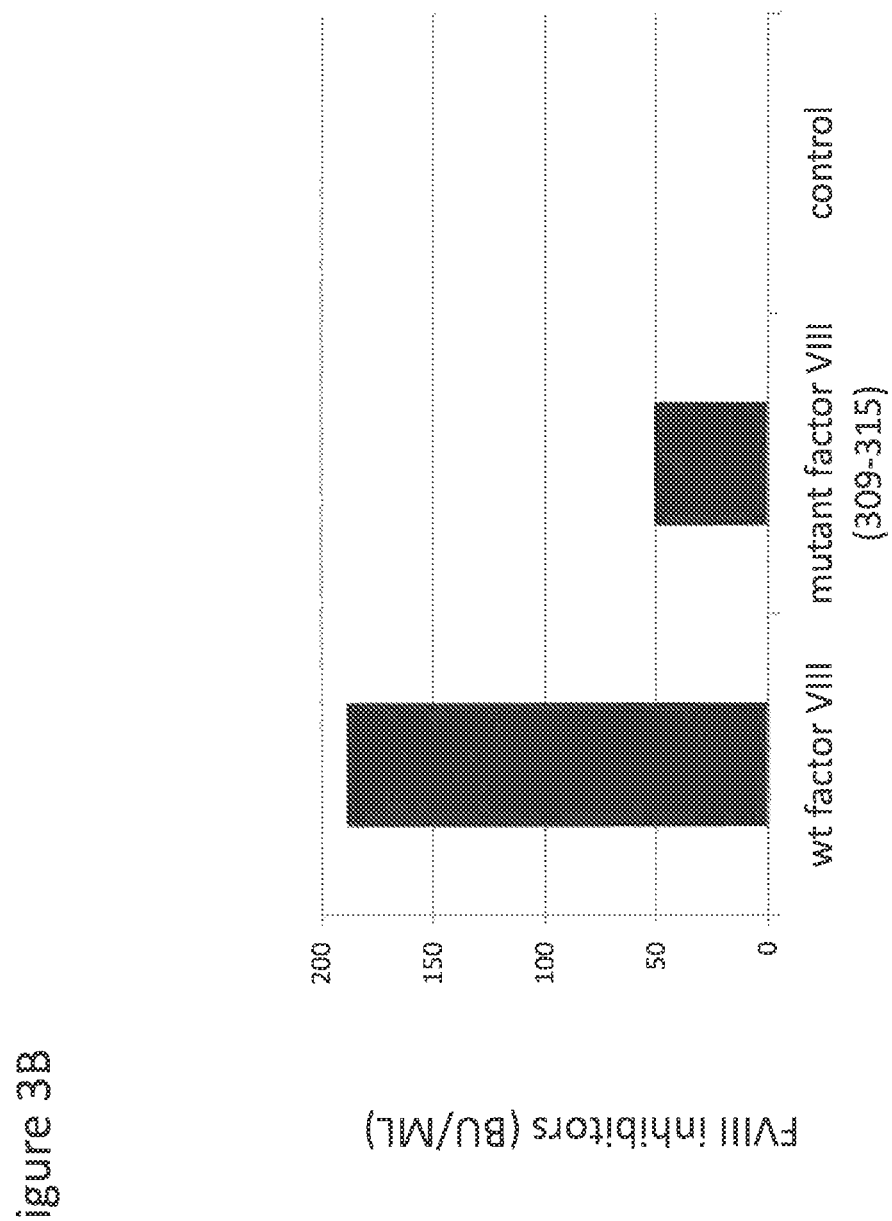
FIG. 3B is a graph of FVII inhibitors (BU) plotted for indicated samples.

FIG. 3A indicates that a 3.6-fold reduction of antibodies was observed in mice injected with the factor VIII mutant F309A-H315A. FIG. 3B shows a 3.8-fold reduction of antibodies inhibiting the function of factor VIII.

These data showed that elimination of a single CD1d binding motif in the factor VIII molecule is sufficient to significanlty reduced the concentration of specific antibodies, including those inhibiting the function of factor VIII.

Example 4

Increased Expression of CD1d on Human Antigen-Presenting Cells Upon Incubation with a Peptide Containing a CD1d-Binding Motif To determine whether human antigen-presenting cells had the capacity to process and present a peptide epitope in the context of the CD1d molecule, the human macrophage cell line U937 was used. Such cells do not express class II major histocompatiblity complexes and are used to assess presentation by CD1d.

The percentage of resting U937 cells expressing CD1d is low as detected with a specific anti-CD1d antibody. It was reasoned that, if U937 cells were incubated with a peptide having the sequence motif enabling it to bind to CD1d, then this should be detectable by increased expression of CD1d at cell surface. As observed for peptides encompassing MHC class II epitopes, the binding of a peptide stabilizes the conformation of the molecule (class II, or CD1d in the present case), allowing the complex to be anchored at cell surface and reducing its intracellular recycling.

U937 cells (7×10$^5$ cells) were incubated for 24h at 37° C. with 5 μg of peptide encompassing CD1d binding motifs or controls. The cells were then washed and incubated with fluorescence-labeled antibodies specific to CD1d and the number of positive cells evaluated using a FACS system.

Figure 4:
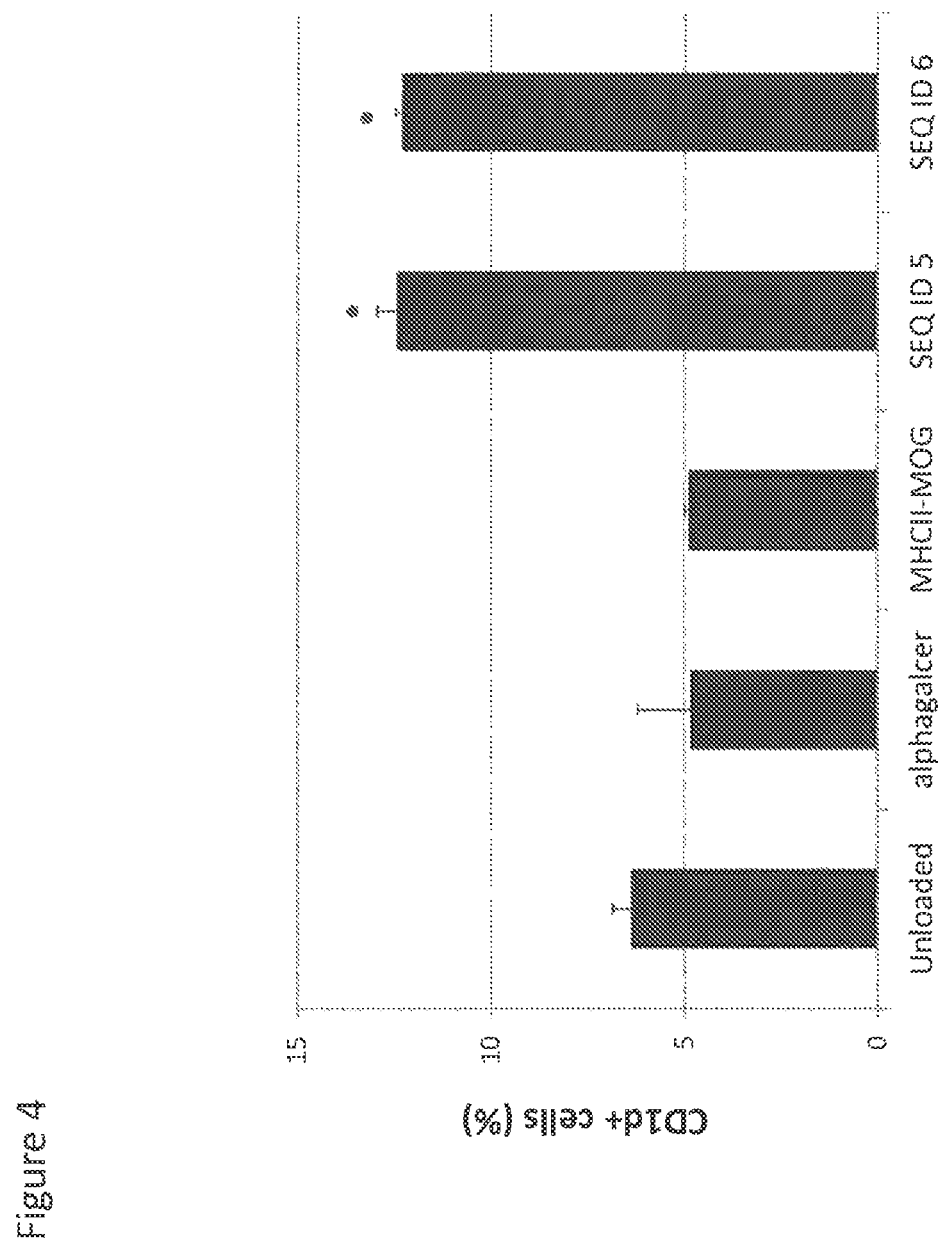
FIG. 4 is a graph of CD1d+ cells (%) plotted for indicated samples.

FIG. 4 shows that the percentage of cells expressing CD1d increases from 6% in control experiments to 13% when peptides containing CD1d-binding sequences were used. Data shown as histograms are means of triplicate measurements, with asterisk identifying results significantly higher than control values ($p<0.05$).

Controls include (from left to right) unloaded U937, cells incubated with alpha-gal-ceramide and a conventional class II-restricted epitope (MHCII-MOG). The experiment includes sequences of factor VIII of either human (SEQ ID NO: 5) or mouse (SEQ ID NO: 6) origin corresponding to aminoacids 188-204 of the factor VIII sequence.

It is therefore concluded that human antigen-presenting cells stabilize complexes of peptides and CD1d at their surface when incubated with said peptides.

Example 5

Human Peripheral Blood Mononucleated Cells (PBMC) Contain NKT Cells Specific for CD1d-Bound Peptidic Epitopes In order to establish whether human PBMC contained cells reacting with a CD1d-binding peptide epitope, invariant NKT (iNKT) cells were prepared from a buffy coat using magnetic beads coated with an antibody specific to the Valpha24-Jalpha18 chain of the T cell receptor (so-called invariant chain).

Said human iNKT cells (10$^5$/condition) were then incubated with mitomycine-C treated U937 cells (Ratio 1:1) loaded with 5 μg of either peptide encompassing aminoacid residues 188-204 of human factor VIII (SEQ ID NO: 5) or with control peptide (MHCII-MOG). Incubation was carried out for 2 weeks at 37° C. in RPMI containing 10% of fetal calf serum and 50 U/ml of human recombinant IL-2.

Figure 5:
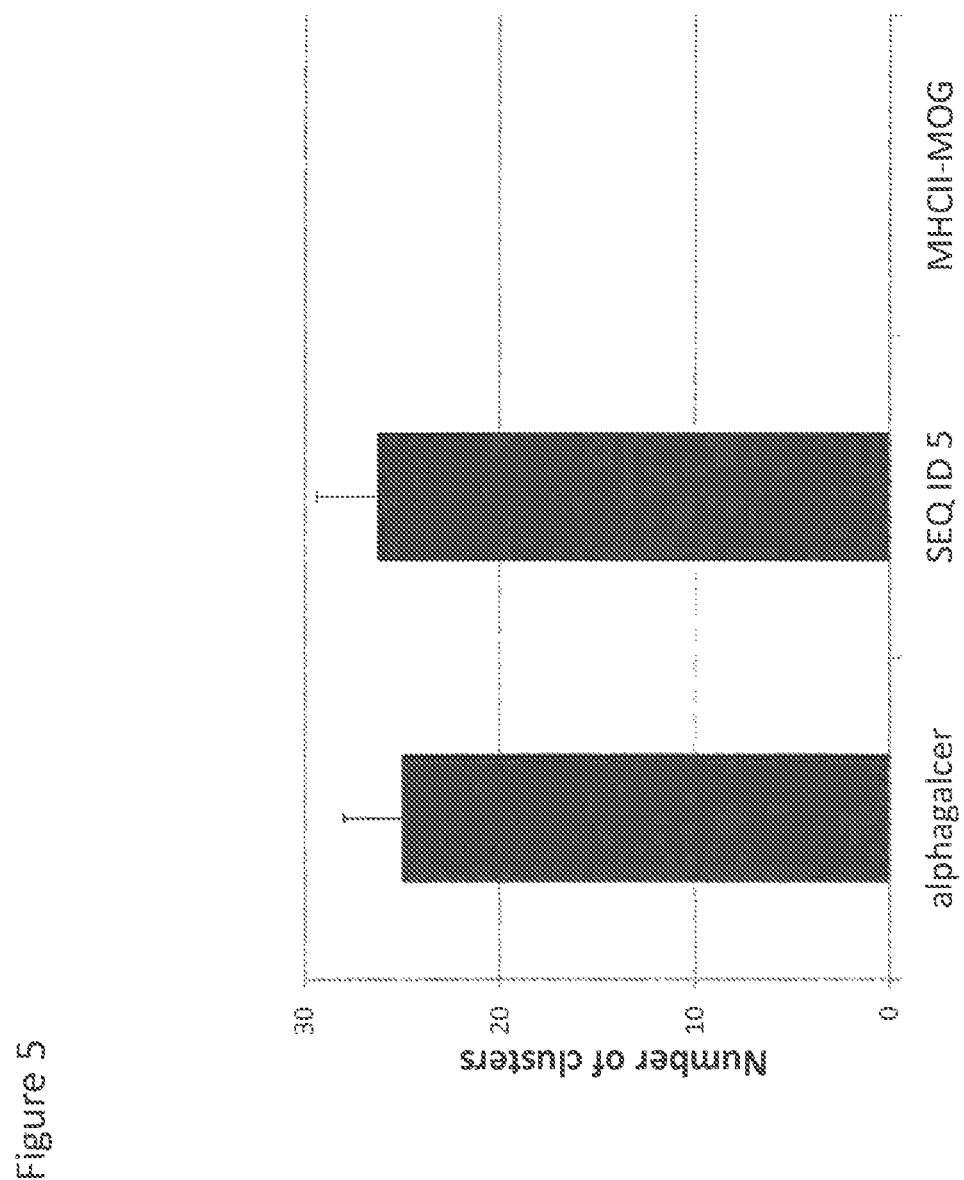
FIG. 5 is a graph of the number of cell clusters observed in indicated samples.

Culture plates were examined by eye for the presence of cell clusters. It is observed that clumps of cells form with U937 loaded with peptide of SEQ ID NO: 5 to the same extent that with alpha-gal-ceramide, but not with control peptide (MHCII-MOG). FIG. 5 illustrates the average of three microscopic field count of this observation (minimum 10 cells/cluster).

It is therefore concluded that human peripheral cell repertoire contains cells defined as invariant chain NKT cells reacting with a peptide presented by CD1d.

Example 6

Flanking Residues Located Outside of the CD Binding Cleft are Important for Efficient Cell Surface Presentation The experiment shown in Example 1 indicates that a peptide of SEQ ID NO: 3, corresponding to human factor VIII aminoacids 190-200, binds to CD tetramers and allows the detection of NKT cells, indicating that this sequence contained the minimum binding motif for CD1d. To determine whether this motif was sufficient for efficient presentation by cells, the experiment reported in example 4 was repeated with peptide of SEQ ID NO: 3.

Figure 6:
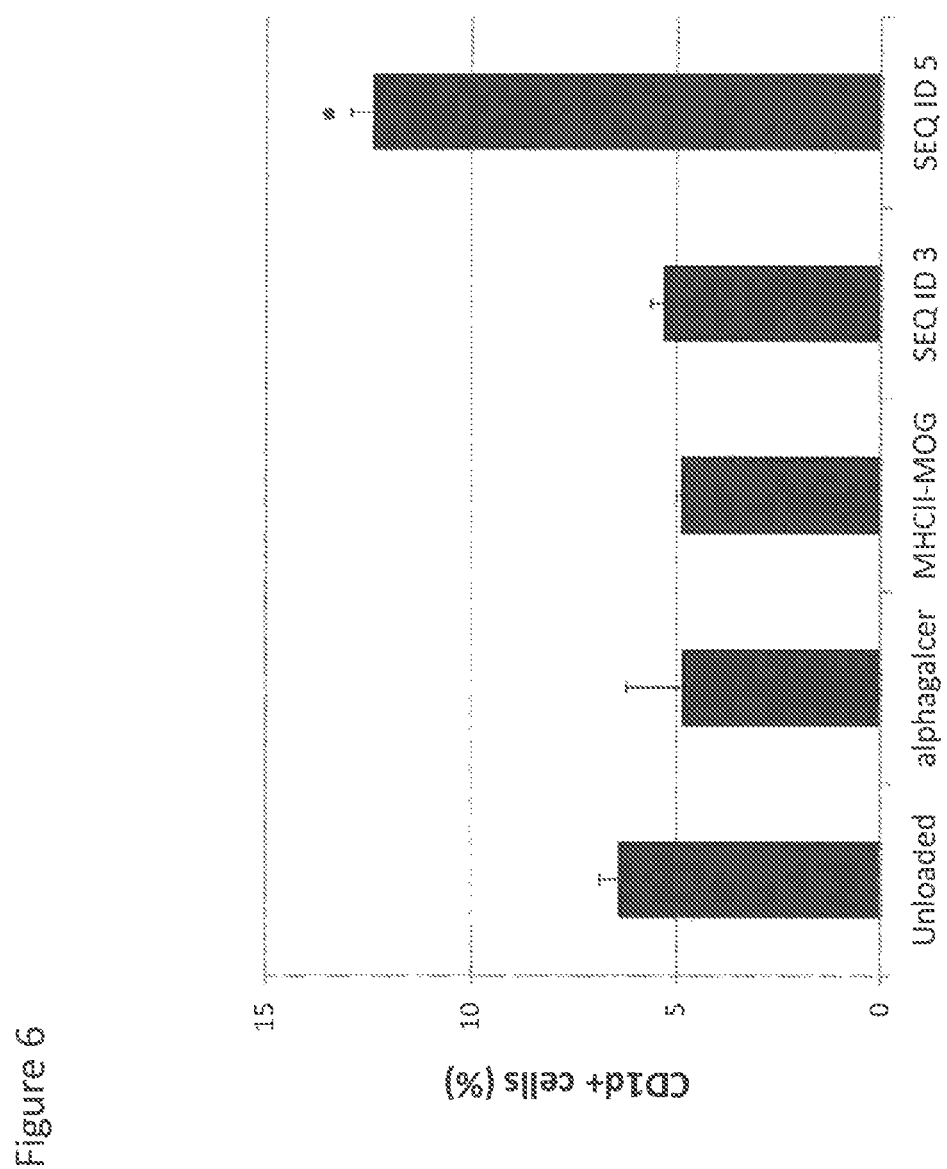
FIG. 6 is a graph of CD1d+ cells (%) plotted for indicated samples.

FIG. 6 shows that peptide of SEQ ID NO: 3 did not increase expression of CD1d at the surface of U937 cells, in contrast to peptides of SEQ ID NO: 5 shown in FIG. 4.

It is therefore concluded that an efficient in vivo loading of a peptide containing a CD1d-binding motif requires the presence of flanking residues located outside of the CD1d cleft.

Example 7

NKT Cells Specific for CD1d-Binding Factor VIII Epitope Belong to Both the CD4+ and CD8+ Lineages To determine the cell lineage to which NKT cells belonged, an experiment was performed as described in Example 2. Thus, JAWS2 cells were loaded with either peptide of SEQ ID NO: 3, B-domain-deleted factor VIII, alpha-gal-ceramide or kept unloaded before intraperitoneal (IP) injection in factor VIII KO mice (2×10$^6$ cells per mouse). Five days after intraperitoneal injections, the mice were sacrificed and the splenocytes prepared. Cell suspensions were then reacted with CD1d tetramers unloaded or loaded with peptide of SEQ ID NO: 3 or with alpha-gal-ceramide.

For faccs analysis, cells binding CD1d tetramers were labeled with DX5- and CD160-specific antibodies and either anti-CD4 or anti-CD8 antibodies. The table summarizes the results.

|    |       |                    | DX5/CD160           | Number of cells (×10$^3$) | |
|----|-------|--------------------|---------------------|------|------|
|    |       |                    | Tetramers           | CD4+ | CD8+ |
| 1  | JAWS2 | (—)                | (—)                 | 0.3  | 0.1  |
| 2  |       |                    | Alpha-gal-cer       | 1.2  | 1.3  |
| 3  |       |                    | Peptide SEQ ID NO: 3 | 39   | 3.5  |
| 4  | JAWS2 | Peptide SEQ ID NO: 3 | (—)               | 0.2  | 0.1  |
| 5  |       |                    | Alpha-gal-cer       | 2.2  | 0.8  |
| 6  |       |                    | Peptide SEQ ID NO: 3 | 47   | 4.1  |
| 7  | JAWS2 | Factor VIII        | (—)                 | 0.1  | 0.5  |
| 8  |       |                    | Alpha-gal-cer       | 1.9  | 1.4  |
| 9  |       |                    | Peptide SEQ ID NO: 3 | 62   | 11   |
| 10 | JAWS2 | Alpha-gal-cer      | (—)                 | 0.1  | 0    |
| 11 |       |                    | Alpha-gal-cer       | 2.3  | 1.8  |
| 12 |       |                    | Peptide SEQ ID NO:3 | 46   | 1.9  |

These experiments show that
- the natural repertoire of NKT cells contains a significant number of cells reacting to peptide of SEQ ID NO: 3 in both the CD4+ and CD8+ lineages (line 3)
- this population of cells can be further expanded by immunization with peptide of SEQ ID NO: 3, again in both CD4+ and CD8+ lineages (line 6)
- immunization with factor VIII is even more efficient in expanding these cell populations (line 9)
- immunization with alpha-gal-ceramide slightly increases the number of CD4+ T cells specific for peptide of SEQ ID NO: 3, but not the number of CD8+ T cells Taken together, these results indicate that immunization with factor VIII elicits an expansion of cells belonging to the NKT lineage of both the CD4+ and CD8+ phenotype.

Sequences
SEQ ID NO: 1    QTLHKFILLFAVFDEGKSWH (human 190-209)

SEQ ID NO: 2    FCHISSHQHDGMEAY (human 309-323)

SEQ ID NO: 3    QTLHKFILLFA (human 190-200)

SEQ ID NO: 4    AVFDEGKSWHS (human 200-210)

SEQ ID NO: 5    KTQTLHKFILLFAVFDE (human 188-204)

SEQ ID NO: 6    RTQMLYQFVLLFAVFDE (mouse 188-204)

The invention claimed is:

1. A method of treating septic shock, acute fibrinolysis, polytrauma, cerebral haemorrhage, or other bleeding disorder, the method comprising administering to a patient in need thereof a factor VIII molecule having a reduced capacity to activate NKT cells and obtained by:

(a) identifying at least one NKT cell epitope comprising SEQ ID NO: 1, SEQ ID NO: 3, or SEQ ID NO:5 in a factor VIII molecule, wherein said epitope comprises a seven amino acid residue sequence (positions P1-P7) being [FWTHY]-$X_2X_3$-[ILMV]-$X_5X_6$-[FWTHY] (SEQ ID NO: 7); and wherein each of $X_2$, $X_3$, $X_5$, and $X_6$ can be any amino acid; and (b) modifying at least one identified NKT cell epitope by substituting the amino acid residue in position P1 with a residue other than F, W, T, H or Y, and by substituting the amino acid residue in position P7 with a residue other than F, W, T, H or Y.

2. The method of claim 1, wherein the factor VIII molecule has a domain structure A1-a1-A2-a2-B-a3-A3-C1-C2, or wherein the Factor VIII is present in plasma with a major form consisting of A1-a1-A2-a2-B linked noncovalently to light chains consisting of A3-C1-C2, in which A1, A2, B, A3, C1 and C2 represent domains and a1, a2 and a3 represent acidic regions linking said domains.

3. The method of claim 1, wherein the factor VIII molecule is obtained by the further step of selecting a modified Factor VIII molecule causing a level of cytokine or of cytolytic agents production upon stimulation of NKT cells of less than 50% of the natural sequence.

4. The method of claim 1, wherein the method is for treating congenital or acquired haemophilia A.

* * * * *

```
                         SEQUENCE LISTING

<160> NUMBER OF SEQ ID NOS: 31

<210> SEQ ID NO 1
<211> LENGTH: 20
<212> TYPE: PRT
<213> ORGANISM: Homo sapiens

<400> SEQUENCE: 1

Gln Thr Leu His Lys Phe Ile Leu Leu Phe Ala Val Phe Asp Glu Gly
1               5                   10                  15

Lys Ser Trp His
            20

<210> SEQ ID NO 2
<211> LENGTH: 15
<212> TYPE: PRT
<213> ORGANISM: homo sapiens

<400> SEQUENCE: 2

Phe Cys His Ile Ser Ser His Gln His Asp Gly Met Glu Ala Tyr
1               5                   10                  15

<210> SEQ ID NO 3
<211> LENGTH: 11
<212> TYPE: PRT
<213> ORGANISM: homo sapiens

<400> SEQUENCE: 3

Gln Thr Leu His Lys Phe Ile Leu Leu Phe Ala
1               5                   10

<210> SEQ ID NO 4
<211> LENGTH: 11
<212> TYPE: PRT
<213> ORGANISM: homo sapiens

<400> SEQUENCE: 4

Ala Val Phe Asp Glu Gly Lys Ser Trp His Ser
1               5                   10

<210> SEQ ID NO 5
<211> LENGTH: 17
<212> TYPE: PRT
<213> ORGANISM: Homo sapiens

<400> SEQUENCE: 5

Lys Thr Gln Thr Leu His Lys Phe Ile Leu Leu Phe Ala Val Phe Asp
1               5                   10                  15

Glu

<210> SEQ ID NO 6
<211> LENGTH: 17
<212> TYPE: PRT
<213> ORGANISM: Mus musculus
```

-continued

<400> SEQUENCE: 6

Arg Thr Gln Met Leu Tyr Gln Phe Val Leu Leu Phe Ala Val Phe Asp
1               5                   10                  15

Glu

<210> SEQ ID NO 7
<211> LENGTH: 7
<212> TYPE: PRT
<213> ORGANISM: Artificial Sequence
<220> FEATURE:
<223> OTHER INFORMATION: NKT epitope
<220> FEATURE:
<221> NAME/KEY: MISC_FEATURE
<222> LOCATION: (1)..(1)
<223> OTHER INFORMATION: X1 = F, W, H, T or Y
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X4 =I, L, M or V
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X7 = F, W, H, T or Y

<400> SEQUENCE: 7

Xaa Xaa Xaa Xaa Xaa Xaa Xaa
1               5

<210> SEQ ID NO 8
<211> LENGTH: 2351
<212> TYPE: PRT
<213> ORGANISM: Homo sapiens

<400> SEQUENCE: 8

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

```
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
            210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
                260                 265                 270
Tyr Trp His Val Ile Gly Met Gly Thr Thr Pro Glu Val His Ser Ile
                275                 280                 285
Phe Leu Glu Gly His Thr Phe Leu Val Arg Asn His Arg Gln Ala Ser
            290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
            370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
```

-continued

Ile Leu Phe Ser Val Phe Asp Glu Asn Arg Ser Trp Tyr Leu Thr Glu
            580                 585                 590
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
        850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
        930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

```
Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Glu Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395
```

-continued

```
Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
```

```
            1790                1795                1800
Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190
```

```
Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 9
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 10-16

<400> SEQUENCE: 9

Phe Leu Cys Leu Leu Arg Phe
1               5

<210> SEQ ID NO 10
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 68-74

<400> SEQUENCE: 10

Thr Leu Phe Val Glu Phe Thr
1               5

<210> SEQ ID NO 11
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 100-106

<400> SEQUENCE: 11

Tyr Asp Thr Val Val Ile Thr
1               5

<210> SEQ ID NO 12
<211> LENGTH: 7
```

```
<212> TYPE: PRT
<213> ORGANISM: Homo sapiens
<220> FEATURE:
<221> NAME/KEY: MISC_FEATURE
<223> OTHER INFORMATION: aa 208-214

<400> SEQUENCE: 12

Thr Gln Thr Leu His Lys Phe
1               5

<210> SEQ ID NO 13
<211> LENGTH: 7
<212> TYPE: PRT
<213> ORGANISM: Homo sapiens

<400> SEQUENCE: 13

His Lys Phe Ile Leu Leu Phe
1               5

<210> SEQ ID NO 14
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 294-300

<400> SEQUENCE: 14

Thr Phe Leu Val Arg Asn His
1               5

<210> SEQ ID NO 15
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 328-334

<400> SEQUENCE: 15

Phe Cys His Ile Ser Ser His
1               5

<210> SEQ ID NO 16
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 336-342

<400> SEQUENCE: 16

His Asp Gly Met Glu Ala Tyr
1               5

<210> SEQ ID NO 17
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 473-479

<400> SEQUENCE: 17

Tyr Gly Glu Val Gly Asp Thr
1               5
```

```
<210> SEQ ID NO 18
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 607-613

<400> SEQUENCE: 18

Thr Glu Asn Ile Gln Arg Phe
1               5

<210> SEQ ID NO 19
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 665-671

<400> SEQUENCE: 19

Thr Asp Phe Leu Ser Val Phe
1               5

<210> SEQ ID NO 20
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 686-692

<400> SEQUENCE: 20

Thr Leu Thr Leu Phe Pro Phe
1               5

<210> SEQ ID NO 21
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 742-748

<400> SEQUENCE: 21

Tyr Glu Asp Ile Ser Ala Tyr
1               5

<210> SEQ ID NO 22
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 1491-1497

<400> SEQUENCE: 22

Tyr Lys Lys Val Glu Asn Thr
1               5

<210> SEQ ID NO 23
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 1805-1811

<400> SEQUENCE: 23
```

```
Tyr Ser Ser Leu Ile Ser Tyr
1               5

<210> SEQ ID NO 24
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 1835-1841

<400> SEQUENCE: 24

Phe Trp Lys Val Gln His His
1               5

<210> SEQ ID NO 25
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 1937-1943

<400> SEQUENCE: 25

Phe His Ala Ile Asn Gly Tyr
1               5

<210> SEQ ID NO 26
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 1998-2004

<400> SEQUENCE: 26

Tyr Pro Gly Val Phe Glu Thr
1               5

<210> SEQ ID NO 27
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 2139-2145

<400> SEQUENCE: 27

Thr Gly Thr Leu Met Val Phe
1               5

<210> SEQ ID NO 28
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 2167-2173

<400> SEQUENCE: 28

Tyr Ile Arg Leu His Pro Thr
1               5

<210> SEQ ID NO 29
<211> LENGTH: 7
<212> TYPE: PRT
<213> ORGANISM: Homo sapiens
```

-continued

<220> FEATURE:
<221> NAME/KEY: MISC_FEATURE
<223> OTHER INFORMATION: aa 2174-2180

<400> SEQUENCE: 29

His Tyr Ser Ile Arg Ser Thr
1 5

<210> SEQ ID NO 30
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 2215-2221

<400> SEQUENCE: 30

Phe Thr Asn Met Phe Ala Thr
1 5

<210> SEQ ID NO 31
<211> LENGTH: 7
<212> TYPE: PRT
<213> ORGANISM: Homo sapiens
<220> FEATURE:
<221> NAME/KEY: MISC_FEATURE
<223> OTHER INFORMATION: aa 2322-2328

<400> SEQUENCE: 31

Thr Arg Tyr Leu Arg Ile His
1 5